(12) United States Patent
Büsing et al.

(10) Patent No.: US 7,790,057 B2
(45) Date of Patent: Sep. 7, 2010

(54) ELECTROLUMINESCENT POLYMERS AND USE THEREOF

(75) Inventors: Arne Büsing, Frankfurt (DE); Holger Heil, Darmstadt (DE); Aurélie Ludemann, Frankfurt (DE); Niels Schulte, Kelkheim (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 12/373,004

(22) PCT Filed: Jun. 22, 2007

(86) PCT No.: PCT/EP2007/005500
§ 371 (c)(1),
(2), (4) Date: Jan. 8, 2009

(87) PCT Pub. No.: WO2008/006454
PCT Pub. Date: Jan. 17, 2008

(65) Prior Publication Data
US 2009/0318625 A1 Dec. 24, 2009

(30) Foreign Application Priority Data
Jul. 11, 2006 (DE) .................. 10 2006 031 991

(51) Int. Cl.
*C09K 11/06* (2006.01)
(52) U.S. Cl. .............. 252/301.16; 252/301.35; 252/700; 345/39; 345/46; 362/545; 362/555; 362/800; 428/690; 428/917; 429/209; 526/256; 526/258; 526/266; 526/270; 526/274; 526/279; 526/280; 526/286; 526/291; 526/310; 528/43; 528/377; 528/380; 528/391; 528/396; 528/403; 528/417; 528/423; 528/425
(58) Field of Classification Search ............ 252/301.16, 252/301.35, 700; 345/39, 46; 362/555, 545, 362/800; 428/690, 917; 429/209; 526/256, 526/258, 266, 270, 279, 280, 286, 291, 310; 528/43, 377, 380, 391, 394, 403, 417, 423, 528/425, 396
See application file for complete search history.

(56) References Cited

U.S. PATENT DOCUMENTS

| | | | |
|---|---|---|---|
| 6,956,095 B2 | 10/2005 | Treacher et al. | |
| 6,994,893 B2 | 2/2006 | Spreitzer et al. | |
| 7,094,897 B2 | 8/2006 | Stossel et al. | |
| 7,125,998 B2 | 10/2006 | Stossel et al. | |
| 7,252,781 B2 | 8/2007 | Spreitzer et al. | |
| 7,288,617 B2 | 10/2007 | Treacher et al. | |
| 7,323,533 B2 | 1/2008 | Becker et al. | |
| 2005/0263758 A1 | 12/2005 | Treacher et al. | |
| 2006/0058494 A1 | 3/2006 | Busing et al. | |
| 2006/0127592 A1 | 6/2006 | Spreitzer et al. | |
| 2006/0127696 A1 | 6/2006 | Stossel et al. | |
| 2006/0149022 A1 | 7/2006 | Parham et al. | |
| 2006/0199943 A1 | 9/2006 | Falcou et al. | |
| 2006/0229427 A1 | 10/2006 | Becker et al. | |
| 2006/0284140 A1 | 12/2006 | Breuning et al. | |
| 2007/0060736 A1 | 3/2007 | Becker et al. | |
| 2007/0080343 A1 | 4/2007 | Heun et al. | |
| 2007/0135635 A1 | 6/2007 | Stössel et al. | |
| 2007/0265473 A1 | 11/2007 | Becker et al. | |
| 2008/0193797 A1 | 8/2008 | Heil et al. | |

FOREIGN PATENT DOCUMENTS

| | | |
|---|---|---|
| DE | 10116962 A1 | 10/2002 |
| DE | 10238903 A1 | 3/2004 |
| DE | 10249723 A1 | 5/2004 |
| DE | 10304819 A1 | 8/2004 |
| DE | 10328627 A1 | 2/2005 |
| DE | 10337077 A1 | 3/2005 |
| DE | 10337346 A1 | 3/2005 |
| DE | 10343606 A1 | 4/2005 |
| DE | 10349033 A1 | 5/2005 |
| DE | 10350606 A1 | 6/2005 |
| EP | 1239526 A2 | 9/2002 |
| GB | 2447172 A | 9/2008 |
| WO | WO-90/13148 A1 | 11/1990 |
| WO | WO-98/39287 A1 | 9/1998 |
| WO | WO-00/46321 A1 | 8/2000 |
| WO | WO-02/068435 A1 | 9/2002 |
| WO | WO-02/072714 A1 | 9/2002 |
| WO | WO-02/077060 A1 | 10/2002 |
| WO | WO-03/019694 A2 | 3/2003 |
| WO | WO-03/020790 A2 | 3/2003 |
| WO | WO-03/048225 A2 | 6/2003 |
| WO | WO-2004/037887 A2 | 5/2004 |
| WO | WO-2007/022845 A1 | 3/2007 |
| WO | WO-2007/055407 A1 | 5/2007 |

OTHER PUBLICATIONS

"Conjugated polymeric electroluminescence element using the same", Database CA, Accession No. 2007:536920, May 18, 2007.
U.S. Appl. No. 12/373,070.

*Primary Examiner*—David Wu
*Assistant Examiner*—Robert Jones, Jr.
(74) *Attorney, Agent, or Firm*—Connolly Bove Lodges Hutz LLP

(57) ABSTRACT

The present invention relates to electroluminescent polymers which contain structural units of the formula (1) and to the use thereof. The polymers according to the invention exhibit improved efficiency and a longer lifetime, in particular on use in polymeric organic light-emitting diodes.

19 Claims, No Drawings

ELECTROLUMINESCENT POLYMERS AND USE THEREOF

The present invention relates to electroluminescent polymers which contain structural units of the formula (1) and to the use thereof. The polymers according to the invention exhibit improved efficiency and a longer lifetime, in particular on use in polymeric organic light-emitting diodes.

Broadly based research into the commercialisation of display and illumination elements based on polymeric (organic) light-emitting diodes (PLEDs) has been underway for more than 10 years. This development was triggered by basic developments which are disclosed in WO 90/13148 A1. A first, albeit simple, product (a small display in a shaver from PHILIPS N.V.) has also recently been available on the market. However, significant improvements in the materials used are still necessary in order to make these displays a true competitor to the liquid-crystal displays (LCDs) which currently dominate the market.

For the production of all three emission colours, it is necessary to copolymerise certain comonomers into the corresponding polymers (cf., for example, WO 00/046321 A1, WO 03/020790 A2 and WO 02/077060 A1). In this way, it is then generally possible, starting from a blue-emitting base polymer ("backbone"), to produce the two other primary colours red and green.

Polymers which have already been proposed or developed for full-colour display elements are various classes of material. Thus, both, for example, polyfluorene derivatives and polyspirobifluorene, polydihydrophenanthrene and polyindenofluorene derivatives are suitable. Polymers which contain a combination of the said structural elements have also already been proposed. In addition, polymers which contain poly-para-phenylene (PPP) as structural element are being employed.

The polymers in accordance with the prior art in some cases already exhibit good properties on use in PLEDs. In spite of the advances that have already been achieved, however, these polymers do not meet the demands made of them for high-quality applications.

In particular, the lifetime of the green- and especially of the blue-emitting polymers is still inadequate for many applications. The same applies to the efficiency of the red-emitting polymers.

Surprisingly, it has now been found that a novel class of polymers has very good properties which are superior to the above-mentioned prior art. The present invention therefore relates to these polymers and to the use thereof in PLEDs. The novel structural units are particularly suitable as polymer backbone, but, depending on the substitution pattern, also as hole conductors, electron conductors and/or emitters.

The invention relates to polymers containing units of the formula (1)

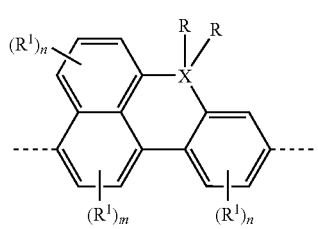

Formula (1)

in which

R is on each occurrence, identically or differently, H, a straight-chain alkyl chain having 1 to 40 C atoms, a branched alkyl chain having 3 to 40 C atoms or a cyclic alkyl chain having 3 to 40 C atoms, each of which may be substituted by $R^1$ and in which, in addition, one or more non-adjacent C atoms may be replaced by $=N-R^1$, $-O-$, $-S-$, $-O-CO-O-$, $-CO-O-$, $-CR^1=CR^1-$ or $-C\equiv C-$ and in which, in addition, one or more H atoms may be replaced by F, Cl, Br, I or CN, or an aromatic ring system having 5 to 40 C atoms or a heteroaromatic ring system having 2 to 40 C atoms, which may also be substituted by one or more radicals $R^1$; the two radicals R here may also form a further mono- or polycyclic, aromatic or aliphatic ring system with one another; preferably with the proviso that at least one or both of the radicals R is (are) not equal to H;

$R^1$ is on each occurrence, identically or differently, H, a straight-chain alkyl chain having 1 to 22 C atoms, a branched alkyl chain having 3 to 22 C atoms or a cyclic alkyl chain having 3 to 22 C atoms, in which, in addition, one or more non-adjacent C atoms may be replaced by $=N-R^2$, $-O-$, $-S-$, $-O-CO-O-$, $-CO-O-$, $-CR^2=CR^2-$ or $-C\equiv C-$ and in which, in addition, one or more H atoms may be replaced by F, Cl, Br, I or CN, or an aryl, heteroaryl, aryloxy or heteroaryloxy group having 5 to 40 C atoms, which may also be substituted by one or more non-aromatic radicals $R^1$; two or more of the radicals $R^1$ here may also form a ring system with one another and/or with R; or F, Cl, Br, I, CN, $N(R^2)_2$, $Si(R^2)_3$ or $B(R^2)_2$;

$R^2$ is on each occurrence, identically or differently, H or an aliphatic or aromatic hydrocarbon radical having 1 to 20 C atoms;

X is on each occurrence, identically or differently, B, C, N, O, P, S, Se, P=O, S=O or $SO_2$;

n is on each occurrence, identically or differently, 0, 1, 2 or 3;

m is on each occurrence, identically or differently, 0, 1 or 2; and the dashed bond in formula (1) and in all other formulae denotes the link in the polymer. It is not intended to represent a methyl group here.

The invention preferably relates to polymers containing units of the formula (1a)

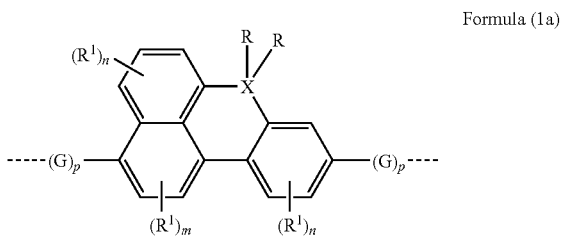

Formula (1a)

in which

R is on each occurrence, identically or differently, H, a straight-chain alkyl chain having 1 to 40 C atoms, a branched alkyl chain having 3 to 40 C atoms or a cyclic alkyl chain having 3 to 40 C atoms, each of which may be substituted by $R^1$ and in which, in addition, one or more non-adjacent C atoms may be replaced by $=N-R^1$, $-O-$, $-S-$, $-O-CO-O-$, $-CO-O-$, $-CR^1=CR^1-$ or $-C\equiv C-$ and in which, in addition, one or more H atoms may be replaced by F, Cl, Br, I or CN, or an aromatic ring system having 5 to 40 C atoms or a heteroaromatic ring system having 2 to 40 C atoms, which may also be substituted by one or more radicals $R^1$; the two radicals R here may also form a further mono- or polycyclic, aromatic or aliphatic ring system with one another; preferably with the proviso that at least one or both of the radicals R is (are) not equal to H;

$R^1$ is on each occurrence, identically or differently, H, a straight-chain alkyl chain having 1 to 22 C atoms, a branched alkyl chain having 3 to 22 C atoms or a cyclic alkyl chain having 3 to 22 C atoms, in which, in addition, one or more non-adjacent C atoms may be replaced by $=N-R^2$, $-O-$, $-S-$, $-O-CO-O-$, $-CO-O-$, $-CR^2=CR^2-$ or $-C\equiv C-$ and in which, in addition, one or more H atoms may be replaced by F, Cl, Br, I or CON, or an aryl, heteroaryl, aryloxy or heteroaryloxy group having 5 to 40 C atoms, which may also be substituted by one or more non-aromatic radicals $R^1$; two or more of the radicals $R^1$ here may also form a ring system with one another and/or with P; or F, Cl, Br, I, CN, $N(R^2)_2$, $Si(R^2)_3$ or $B(R^2)_2$;

$R^2$ is on each occurrence, identically or differently, H or an aliphatic or aromatic hydrocarbon radical having 1 to 20 C atoms;

X is on each occurrence, identically or differently, B, C, N, O, P, S, Se, $P=O$, $S=O$ or $SO_2$;

G is on each occurrence identical or different and stands for a divalent unit selected from group 1, group 2, group 3, group 4, group 5, group 6, group 7 or a mixture of a plurality of groups 1 to 7;

n is on each occurrence, identically or differently, 0, 1, 2 or 3;

m is on each occurrence, identically or differently, 0, 1 or 2;

p is on each occurrence, identically or differently, 0 or 1; and the dashed bond in formula (1a) and in all other formulae denotes the link in the polymer. It is not intended to represent a methyl group here.

Although this is evident from the description, it should again be explicitly pointed out here that the structural units of the formulae (1) and (1a) may be asymmetrically substituted, i.e. different substituents R or $R^1$ may be present on a single unit.

For the purposes of the present invention, an aromatic or heteroaromatic ring system is intended to be taken to mean a system which does not necessarily contain only aromatic or heteroaromatic groups respectively, but instead in which a plurality of aromatic or heteroaromatic groups may also be interrupted by a short non-aromatic unit (<10% of the atoms other than H, preferably <5% of the atoms other than H), such as, for example, hybridised C, O, N, etc. Thus, for example, systems such as, for example, 9,9'-spirobifluorene, 9,9-diarylfluorene, triarylamine, etc., are also intended to be taken to mean aromatic ring systems in the present application.

The polymer according to the invention usually contains at least 5 mol %, preferably at least 10 mol %, particularly preferably at least 30 mol % and in particular at least 50 mol %, of units of the formula (1) or (1a). It has been found that if different units of the formula (1) or (1a) are present simultaneously, the sum of all units of the formulae (1) and (1a) is in the above-mentioned range, so that the content of individual units of the formulae (1) and (1a) in such cases may also be less than 5 mol %.

The polymers according to the invention are conjugated or partially conjugated polymers.

For the purposes of the present application, conjugated polymers are polymers which contain in the main chain principally $sp^2$-hybridised carbon atoms, which may also be replaced by corresponding heteroatoms. In the simplest case, this means the alternating presence of double and single bonds in the main chain. Principally means that naturally occurring defects which result in conjugation interruptions do not devalue the term "conjugated polymer". Furthermore, the term conjugated is likewise used in this application text if, for example, arylamine units and/or certain heterocycles (i.e. conjugation via N, O or S atoms) and/or organometallic complexes (i.e. conjugation via the metal atom) are located in the main chain.

By contrast, units such as, for example, simple alkyl bridges, (thio)ether, ester, amide or imide links are clearly defined as non-conjugated segments. A partially conjugated polymer is intended to be taken to mean a polymer in which extended conjugated sections in the main chain are interrupted by non-conjugated sections, or which contains extended conjugated sections in the side chains of a polymer which is non-conjugated in the main chain.

Besides the units of the formula (1) or (1a), the polymers according to the invention may also contain further structural elements. These are, inter alia, those disclosed and extensively listed in WO 02/077060 A1 and in DE 10337346 A1. These are regarded as part of the present application by way of reference. The other structural units may originate, for example, from the following classes:

Group 1: units which enhance the hole-injection and/or -transport properties of the polymers;

Group 2: units which enhance the electron-injection and/or -transport properties of the polymers;

Group 3: units which have combinations of individual units from group 1 and group 2;

Group 4: units which modify the emission characteristics to such an extent that electrophosphorescence can be obtained instead of electrofluorescence;

Group 5: units which improve the transition from the so-called singlet state to the triplet state;

Group 6: units which influence the morphology and/or emission colour of the resultant polymers;

Group 7: units which are typically used as backbone.

Preferred polymers according to the invention are those in which at least one structural element has charge-transport properties, i.e. which contain units from groups 1 and/or 2.

Structural elements from group 1 which have hole-transport properties are, for example, triarylamine, benzidine, tetraaryl-para-phenylenediamine, tri-arylphosphine, phenothiazine, phenoxazine, dihydrophenazine, thianthrene, dibenzo-para-dioxin, phenoxathiyne, carbazole, azulene, thiophene, pyrrole and furan derivatives and further O-, S- or N-containing heterocycles having a high HOMO (HOMO=highest occupied molecular orbital). These arylamines and heterocycles preferably result in an HOMO in the polymer of greater than −5.8 eV (against vacuum level), particularly preferably greater than −5.5 eV.

Structural elements from group 2 which have electron-transport properties are, for example, pyridine, pyrimidine, pyridazine, pyrazine, oxadiazole, quinoline, quinoxaline and phenazine derivatives, but also triarylboranes and further O-, S- or N-containing heterocycles having a low LUMO (LUMO=lowest unoccupied molecular orbital). These units in the polymer preferably result in an LUMO of less than −2.7 eV (against vacuum level), particularly preferably less than −3.0 eV.

It may be preferred for the polymers according to the invention to contain units from group 3 in which structures which increase the hole mobility and which increase the electron mobility (i.e. units from groups 1 and 2) are bonded directly to one another. Some of these units may serve as emitters and shift the emission colour into the green, yellow or red. Their use is thus suitable, for example, for the production of other emission colours from originally blue-emitting polymers.

Structural elements from group 4 are those which, even at room temperature, are able to emit light from the triplet state with high efficiency, i.e. exhibit electrophosphorescence instead of electrofluorescence, which frequently causes an increase in the energy efficiency. Suitable for this purpose are firstly compounds which contain heavy atoms having an atomic number of greater than 36. Preference is given to compounds which contain d or f transition metals which satisfy the above-mentioned condition. Particular preference is given here to corresponding structural units which contain elements from groups 8 to 10 (Ru, Os, Rh, Ir, Pd, Pt). Suitable structural units for the polymers according to the invention here are, for example, various complexes, as described, for example, in WO 02/068435 A1, DE 10116962 A1, EP 1239526 A2 and DE 10238903 A1. Corresponding monomers are described in WO 02/068435 A1 and DE 10350606 A1.

Structural elements from group 5 are those which improve the transition from the singlet state to the triplet state and which, employed in support of the structural elements from group 4, improve the phosphorescence properties of these structural elements. Suitable for this purpose are, in particular, carbazole and bridged carbazole dimer units, as described in DE 10304819 A1 and DE 10328627 A1. Also suitable for this purpose are ketones, phosphine oxides, sulfoxides and similar compounds, as described in DE 10349033 A1.

Besides those mentioned above, structural elements from group 6 which influence the morphology and/or emission colour of the polymers are those which have at least one further aromatic or other conjugated structure which does not fall under the above-mentioned groups, i.e. those which have only little influence on the charge-carrier mobilities, are not organo-metallic complexes or have no influence on the singlet-triplet transition. Structural elements of this type may influence the morphology and/or emission colour of the resultant polymers. Depending on the unit, they can therefore also be employed as emitters. Preference is given here to aromatic structures having 6 to 40 C atoms or also tolan, stilbene or bisstyryl-arylene derivatives, each of which may be substituted by one or more radicals $R^1$. Particular preference is given here to the incorporation of 1,4-phenylene, 1,4-naphthylene, 1,4- or 9,10-anthrylene, 1,6-, 2,7- or 4,9-pyrenylene, 3,9- or 3,10-perylenylene, 4,4'-biphenylylene, 4,4"-terphenylene, 4,4'-bi-1,1'-naphthylylene, 4,4'-tolanylene, 4,4'-stilbenzylene or 4,4"-bisstyrylarylene derivatives.

Structural elements from group 7 are units containing aromatic structures having 6 to 40 C atoms which are typically used as polymer backbone. These are, for example, 4,5-dihydropyrene derivatives, 4,5,9,10-tetrahydropyrene derivatives, fluorene derivatives, 9,9'-spirobifluorene derivatives, 9,10-dihydrophenanthrene derivatives, 5,7-dihydrodibenzooxepine derivatives and cis- and trans-indenofluorene derivatives. However, since the proportion of units of the formula (1) or (1a) is, in particular, at least 50 mol %, these structural elements from group 7 are preferably not employed here as the principal polymer backbone, but at most as a backbone which is present in a smaller proportion.

Preference is given to polymers according to the invention which, besides structural units of the formula (1) or (1a), simultaneously additionally also contain one or more units selected from groups 1 to 7. It may likewise be preferred for more than one structural unit from a group to be present at the same time.

The proportion of units of the formula (1) or (1a) is preferably at least 10 mol %, particularly preferably at least 30 mol % and in particular at least 50 mol %. This preference applies, in particular, if the units of the formula (1) or (1a) are the polymer backbone. In the case of other functions, other proportions may be preferred, for example a proportion in the order of 5 to 20 mol % in the case of the hole conductor or emitter in an electroluminescent polymer. For other applications, for example for organic transistors, the preferred proportion may again be different, for example up to 100 mol % in the case of hole- or electron-conducting units.

Preference is given to polymers according to the invention which, apart from structural units of the formula (1) or (1a), also contain at least one structural unit from the above-mentioned groups. At least two structural units are particularly preferably from different classes of those mentioned above. If present, the proportion of these structural elements is preferably in each case at least 5 mol %, particularly preferably in each case at least 10 mol %. Particularly, one of these structural units is selected from the group of the hole-conducting units and the other group is an emitting unit, where these two functions (hole conduction and emission) may also be taken on by the same unit.

However, a smaller proportion of the emitting units, in particular green- and red-emitting units, may also be preferred, for example for the synthesis of white-emitting copolymers. The way in which white-emitting copolymers can be synthesised is described in detail in DE 10343606 A1.

The polymers according to the invention preferably have 10 to 10,000, particularly preferably 50 to 5000 and in particular 50 to 2000 recurring units.

The requisite solubility of the polymers is ensured, inter alia, by the substituents R and $R^1$ on the units of the formula (1) or (1a) and optionally on further units present. If further substituents are present, these may also contribute to the solubility.

In order to ensure adequate solubility, it is preferred for at least 2 non-aromatic C atoms to be present in the substituents on average per recurring unit. Preference is given here to at least 4 and particularly preferably at least 8 C atoms. Individual C atoms thereof may also be replaced by O or S. However, it is entirely possible for this to mean that a certain proportion of recurring units does not carry any further non-aromatic substituents.

In order to avoid impairing the morphology of the film, it is preferred to have no long-chain substituents having more than 12 C atoms in a linear chain, particularly preferably none having more than 8 C atoms and in particular none having more than 6 C atoms.

Non-aromatic C atoms are, as, for example, in the description of R and $R^1$ in formula (1) or (1a), present in corresponding straight-chain, branched or cyclic alkyl or alkoxy chains.

Preference is given to polymers according to the invention in which, for units of the formula (1) or (1a),
R on each occurrence, identically or differently, denotes a straight-chain alkyl chain having 1 to 25 C atoms, a branched alkyl chain having 3 to 25 C atoms or a cyclic alkyl chain having 3 to 25 C atoms, in which, in addition, one or more non-adjacent C atoms may be replaced by =N—$R^1$, —O—, —S—, —O—CO—O—, —CO—O—, —CH=CH— or —C≡C— and in which, in addition, one or more H atoms may be replaced by F or CN, or an aromatic ring system having 5 to 20 C atoms or a heteroaromatic ring system having 2 to 20 C atoms, which may also be substituted by one or more non-aromatic radicals $R^1$; the two radicals R here may also form a further mono- or polycyclic, aromatic or aliphatic ring system with one another;

$R^1$ on each occurrence, identically or differently, denotes H, a straight-chain alkyl chain having 1 to 22 C atoms, a branched alkyl chain having 3 to 22 C atoms or a cyclic alkyl chain having 3 to 22 C atoms, in which, in addition, one or more non-adjacent C atoms may be replaced by =N—$R^2$—O—, —S—, —O—CO—O—, —CO—O—, —CH=CH— or —C≡C— and in which, in addition, one or more H atoms may be replaced by F or CN, or an aryl, heteroaryl, aryloxy or heteroaryloxy group having 5 to 40 C atoms, which may also be substituted by one or more non-aromatic radicals $R^1$; two or more of the radicals $R^1$ here may also form a mono- or polycyclic, aliphatic or aromatic ring system with one another and/or with R; or F, Cl, Br, I, CN, $N(R^2)_2$, $Si(R^2)_3$ or $B(R^2)_2$; and X is on each occurrence, identically or differently, B, C, N, O, P, S, P=O, S=O or $SO_2$.

Particular preference is given to polymers according to the invention in which, for units of the formula (1) or (1a), R is on each occurrence, identically or differently, a straight-chain, branched or cyclic alkyl chain having 4 to 20 C atoms, particularly preferably a branched alkyl chain, in which, in addition, one or more non-adjacent C atoms may be replaced by =N—$R^1$, —O—, —S—, —O—CO—O—, —CO—O—, —CH=CH— or —C≡C— and in which, in addition, one or more H atoms may be replaced by F; the two radicals R here may also form a further mono- or polycyclic ring system with one another;

X is on each occurrence C; and p stands for the number zero.

The preference for aliphatic radicals R can be explained by the still better solubility of the resultant polymers and the better synthetic accessibility.

Depending on the substitution pattern, the units of the formula (1) or (1a) are particularly suitable for various functions in the polymer. Thus, these units can preferably be employed as (electron-conducting) polymer backbone, as hole conductors or as emitters.

Preference is furthermore given to units of the formula (1) or (1a) which are symmetrically substituted in the 7,7'-positions. This preference can be explained by the better synthetic accessibility of the monomers. It is thus preferred for all R in a unit of the formula (1) or (1a) to be identical and particularly preferably also to be identically substituted.

Examples of preferred units of the formula (1) or (1a) are the following structures, where the linking in the polymer in each case takes place via the 3,9-positions, as indicated by the dashed bonds. For clarity, possible substituents are generally not shown or not shown everywhere. Alkyl here generally stands for an aliphatic alkyl group, aryl for an aromatic or hetero-aromatic system, as described for R.

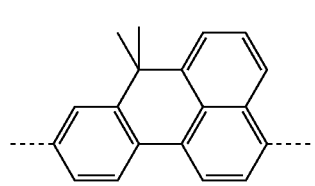

Formula 1

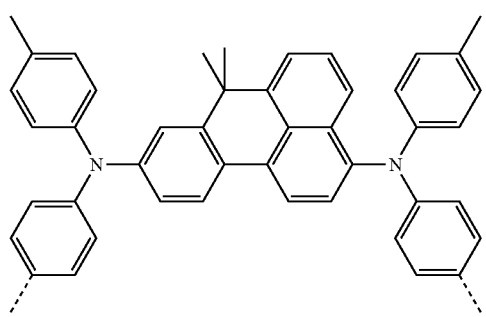

Formula 2

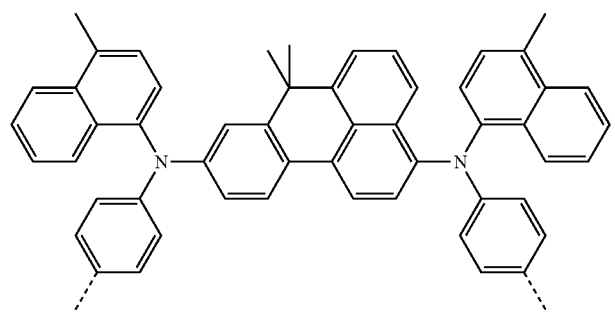

Formula 3

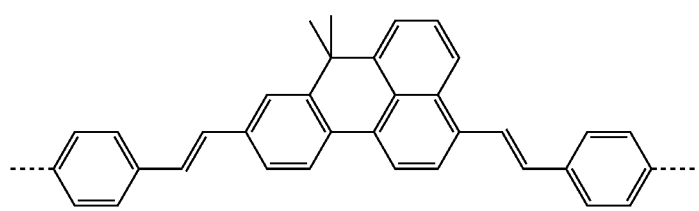

Formula 4

-continued
Formula 5
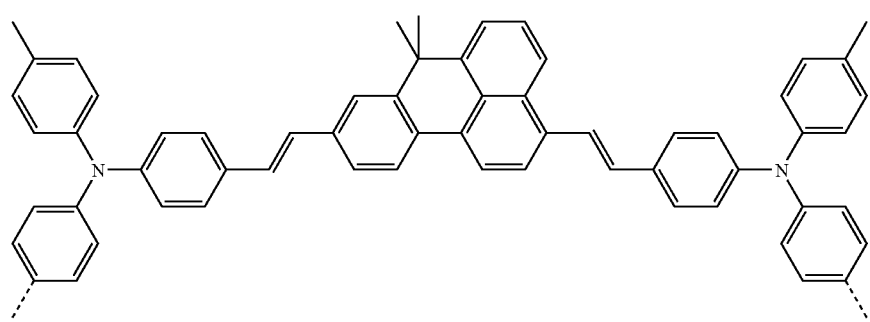
Formula 6
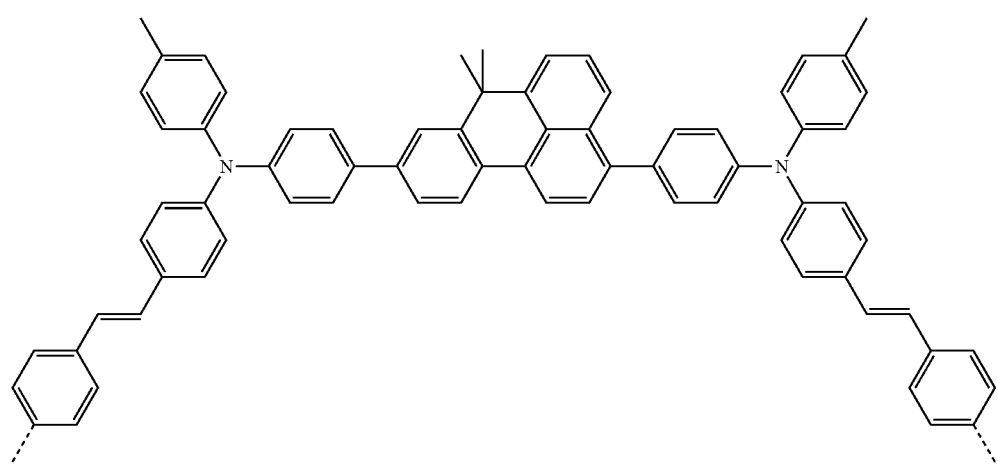
Formula 7
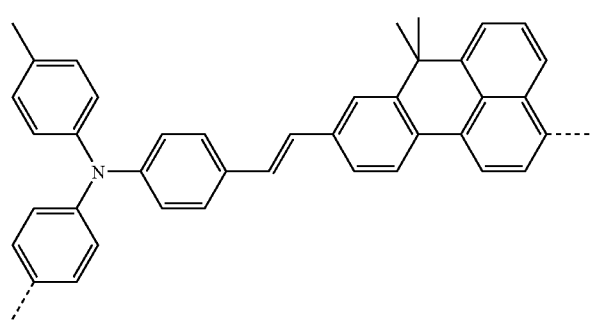
Formula 8
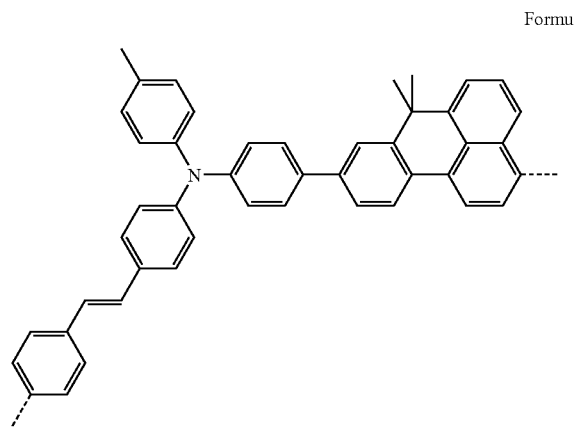
Formula 9
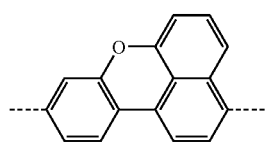

Formula 10

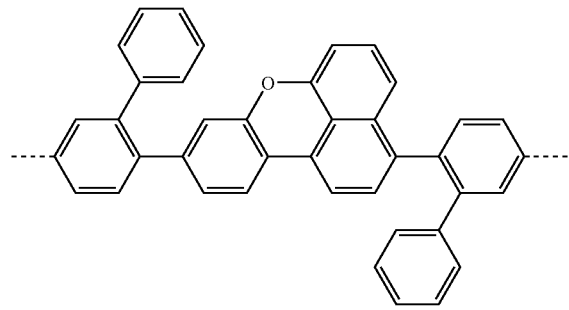

Formula 11

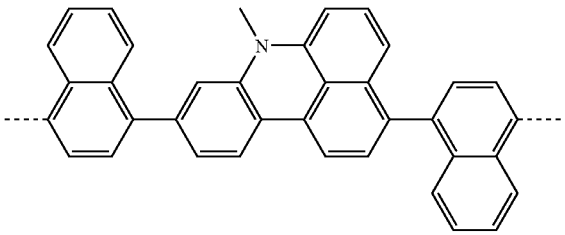

Formula 12

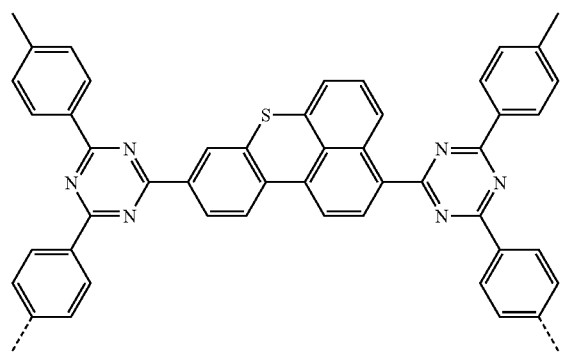

Formula 13

Formula 14

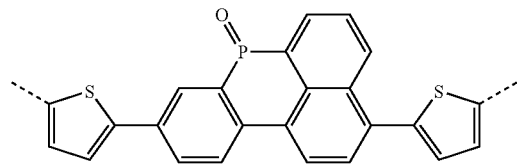

The polymers according to the invention are either homopolymers or copolymers. Besides one or more structures of the formula (1) or (1a), copolymers according to the invention can potentially contain one or more further structures, for example from the above-mentioned groups 1 to 7.

The copolymers according to the invention can contain random, alternating or block-like structures or also have a plurality of these structures in an alternating arrangement. The way in which copolymers having block-like structures can be obtained is described in detail, for example, in DE 10337077 A1. This laid-open specification is part of the present application by way of reference.

Properties such as solubility, solid-phase morphology, colour, charge-injection and -transport properties, temperature stability, electro-optical characteristics, etc., can be adjusted by the use of a plurality of different structural elements.

The polymers according to the invention are generally prepared by polymerisation of one or more types of monomer, of which at least one monomer results in units of the formula (1) or (1a) in the polymer. There are in principle many corresponding polymerisation reactions. However, some types which result in C—C or C—N links have proven particularly successful here:

(A) SUZUKI polymerisation;

(B) YAMAMOTO polymerisation;

(C) STILLE polymerisation;

(D) HARTWIG-BUCHWALD polymerisation.

The way in which the polymerisation can be carried out by these methods and the way in which the polymers can be separated off from the reaction medium and purified is described in detail, for example, in DE 10249723 A1.

Monomers which result in structural units of the formula (1) in the polymers according to the invention are derivatives which have in the 3,9-position suitable functionalities which allow this monomer unit to be incorporated into the polymer. If another link is desired, the functionality must be correspondingly modified.

Monomers which result in units of the formula (1) or (1a) in the polymer are novel and are therefore likewise a subject-matter of the present invention.

The invention thus furthermore relates to bifunctional monomeric compounds of the formula (2) or (2a)

Formula (2)

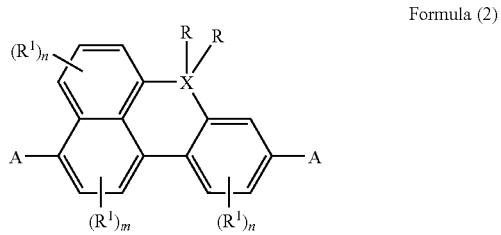

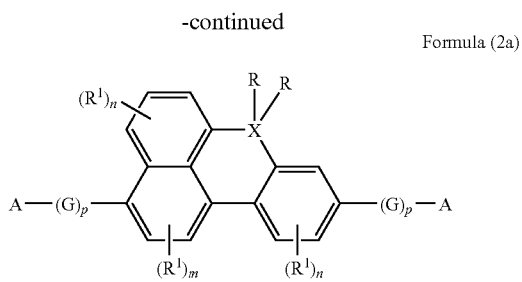

Formula (2a)

which are characterised in that the two functional groups A, identically or differently, copolymerise under conditions of C—C or C—N linking reactions, where the other symbols and indices have the same meaning as in relation to formula (1) or (1a).

A is preferably selected from Cl, Br, I, O-tosylate, O-triflate, O—SO$_2$R$^2$, B(OR$^2$)$_2$ and Sn(R$^2$)$_3$, particularly preferably from Br, I and B(OR$^2$)$_2$, where R$^2$ has the same meaning as described above, and where two or more radicals R$^2$ may also form a ring system with one another.

The C—C linking reactions are preferably selected from the groups of the SUZUKI coupling, the YAMAMOTO coupling and the STILLE coupling; the C—N linking reaction is preferably a HARTWIG-BUCHWALD coupling.

The same preference as described above for the structural units of the formula (1) or (1a) applies to bifunctional monomeric compounds of the formula (2) or (2a).

It may be preferred not to use the polymer according to the invention as the pure substance, but instead as a mixture (blend) together with any desired further polymeric, oligomeric, dendritic or low-molecular-weight substances. These may, for example, improve the electronic properties, influence the transfer from the singlet state to the triplet state or themselves emit light from the singlet state or from the triplet state. Electronically inert substances may, however, also be appropriate in order, for example, to influence the morphology of the polymer film formed or the viscosity of polymer solutions. The present invention therefore also relates to blends of this type.

The invention furthermore relates to solutions and formulations of one or more polymers or blends according to the invention in one or more solvents. The way in which polymer solutions can be prepared is described, for example, in WO 02/072714 A1, in WO 03/019694 A2 and in the literature cited therein. These solutions can be used to produce thin polymer layers, for example by surface coating methods (for example spin coating) or printing processes (for example ink-jet printing).

The polymers according to the invention can be used in PLEDs. These comprise cathode, anode, emission layer and optionally further layers, such as, for example, preferably a hole-injection layer and optionally an interlayer between the hole-injection layer and the emission layer. The way in which PLEDs can be produced is described in detail as a general process in DE 10304819 A1, which should be adapted correspondingly for the individual case.

As described above, the polymers according to the invention are very particularly suitable as electroluminescent materials in the PLEDs or displays produced in this way.

For the purposes of the invention, electroluminescent materials are taken to mean materials which can be used as the active layer in a PLED. Active layer means that the layer is capable of emitting light on application of an electric field (light-emitting layer) and/or that it improves the injection and/or transport of the positive and/or negative charges (charge-injection or charge-transport layer). It may also be an interlayer between a hole-injection layer and an emission layer.

The invention therefore also relates to the use of a polymer according to the invention in a PLED, in particular as electroluminescent material.

The invention thus likewise relates to a PLED having one or more active layers, where at least one of these active layers comprises one or more polymers according to the invention. The active layer can be, for example, a light-emitting layer and/or a transport layer and/or a charge-injection layer and/or an interlayer.

The polymers according to the invention have the following surprising advantages over the polyspirobifluorenes and polyfluorenes described in WO 03/020790 A2 and WO 02/077060 A1, which are hereby named as closest prior art:

(1) It has been found that the polymers according to the invention (with otherwise identical or similar composition) have higher luminous efficiencies in the application. This applies, in particular, to the copolymers which exhibit blue emission. This is of enormous importance since either the same luminance can thus be achieved with lower energy consumption, which is very important, in particular, in mobile applications (displays for mobile phones, pagers, PDAs, etc.), which are reliant on standard or rechargeable batteries. Conversely, higher luminances are obtained with the same energy consumption, which may be interesting, for example, for illumination applications.

(2) It has furthermore been found, surprisingly, that, again in direct comparison, the polymers according to the invention have longer operating lifetimes, in particular in the case of green- and blue-emitting PLEDs.

(3) Even without the use of electron-conducting comonomers, the polymers according to the invention are good electron conductors. Electron-conducting properties in polymers have hitherto been difficult to achieve since many electron conductors in accordance with the prior art are not sufficiently stable for high-quality applications.

The present application text and also the examples below are directed to the use of polymers or blends according to the invention in relation to PLEDs and the corresponding displays. In spite of this restriction of the description, it is possible for the person skilled in the art, without further inventive step, also to use the polymers according to the invention for further uses in other electronic devices, for example for organic integrated circuits (O-ICs), organic field-effect transistors (OFETs), organic thin-film transistors (OTFTs), organic solar cells (O-SCs) or also organic laser diodes (O-lasers), to mention but a few applications.

The present application likewise relates to the use of polymers according to the invention in the corresponding devices and to these devices themselves.

The present invention is explained in greater detail below with reference to working examples, but without being restricted thereby.

EXAMPLES

Example 1

Preparation of 3,9-dibromo-7,7-dimethyl-7H-benzo[de]anthracene

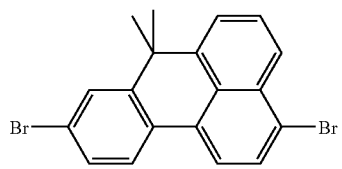

1.1 Preparation of 3,9-dibromobenzo[de]anthracen-7-one

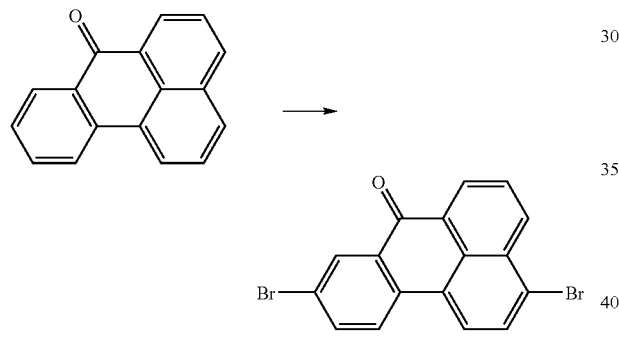

50 g (217 mmol) of benzanthrone are initially introduced in 800 ml of nitrobenzene and brought to an internal temperature of 90° C. 25 ml (490 mmol) of bromine, dissolved in 100 ml of nitrobenzene, are added dropwise over the course of 30 minutes. The reaction mixture is then heated to an internal temperature of 150° C. After 2 hours, the mixture is cooled to room temperature, 200 ml of EtOH are added dropwise, the yellow precipitate is filtered off with suction, washed with copious EtOH and dried, giving 49.7 g (59%) of the dibrominated product as yellow powder.

1.2 Preparation of 3,9-dibromo-7H-benzo[de]anthracene

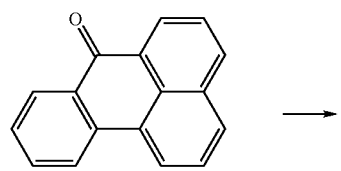

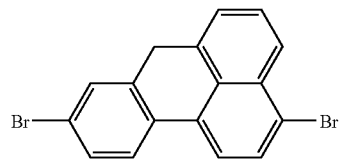

37.17 g (81.7 mmol) of dibromobenzanthrone and 10.9 g (81.7 mmol) of AlCl$_3$ are initially introduced under N$_2$ in 330 ml of dried diethyl ether into an apparatus which has been dried by heating. 3.1 g (81.7 mmol) of LiAlH$_4$ in 400 ml of ether (dissolved or suspended in advance with ice-cooling under N$_2$) are then added dropwise with ice-cooling. When the addition is complete, the mixture is heated at the boil for a further 60 minutes.

10 ml of ethyl acetate are slowly added with ice-cooling, 100 ml of 6 M HCl are subsequently carefully added dropwise, and the resultant precipitate is filtered off with suction, washed with 1 M HCl and MeOH and dried by suction, giving 25.6 g (84%) of a pale-yellow solid.

1.3 Preparation of 3,9-dibromo-7,7-dimethyl-7H-benzo[de]anthracene

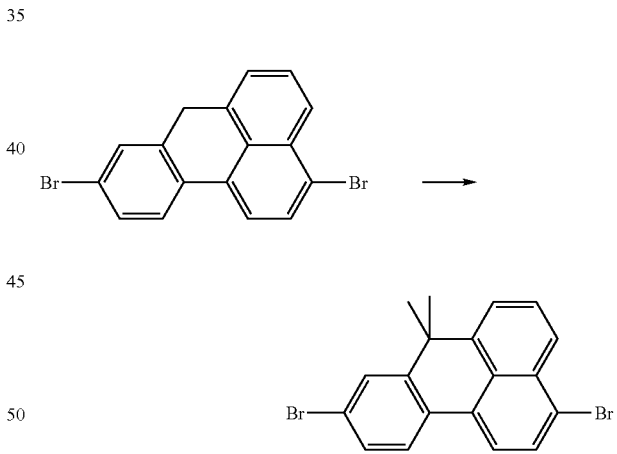

26 g (69 mmol) of 3,9-dibromo-7H-benzo[de]anthracene are dissolved in 280 ml of dried DMSO at 70° C., 40 g (416 mmol) of NaO$^t$Bu are added, and the suspension is heated to an internal temperature of 80° C. 25.9 ml (416 mmol) of methyl iodide are slowly added dropwise at this temperature (1 hour, temperature <90° C.). The internal temperature is then held at 80 to 90° C. for a further 1.5 hours. The cooled batch is poured into 1000 ml of ice-water, and the mixture is stirred for 20 minutes, the resultant solid is filtered off with suction, washed with water and MeOH and recrystallised six times from toluene, giving a pale-yellow solid having a purity of >99.9% in a yield of 77% (21.4 g).

Example 2

Synthesis of Further Monomers

The synthesis of the further monomers M2 to M5 described below is described in WO 03/020790 and the literature cited therein.

Monomer M2

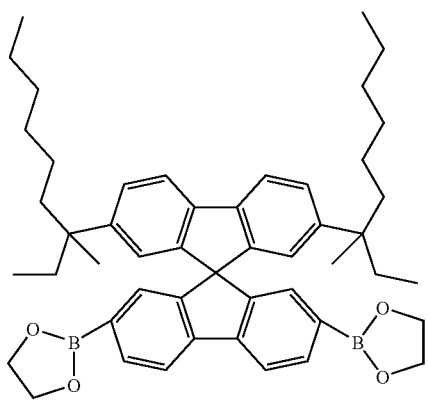

Monomer M3

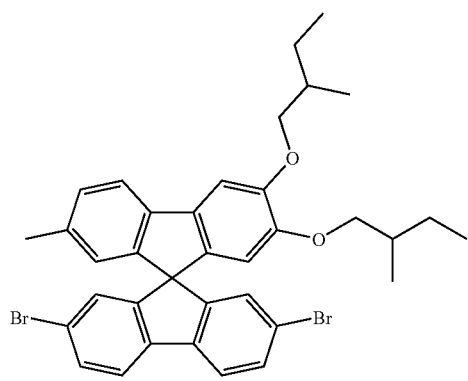

Monomer M4

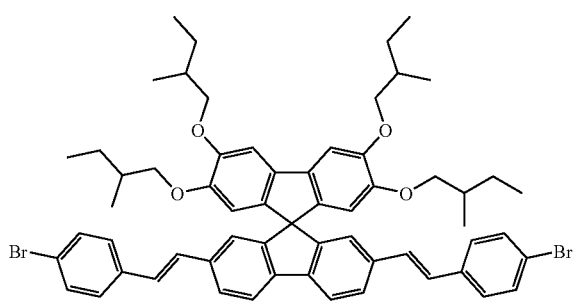

Monomer M5

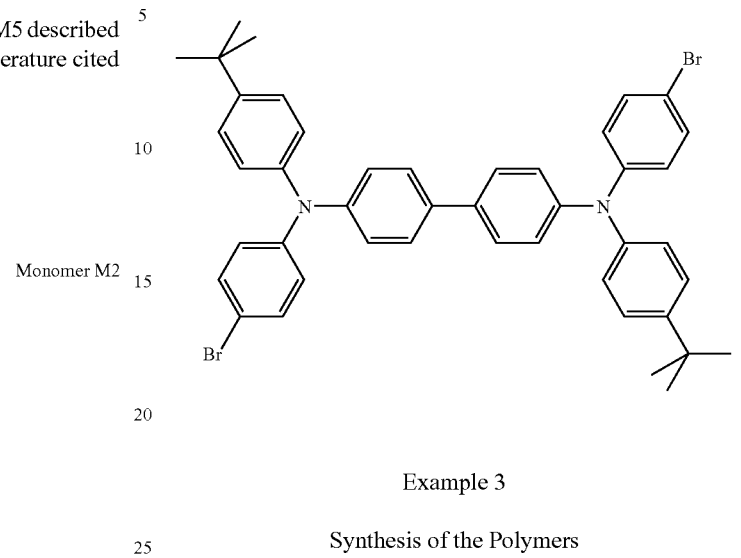

Example 3

Synthesis of the Polymers

The polymers according to the invention and the comparative polymers are synthesised by SUZUKI coupling as described in WO 03/048225. The composition of the synthesised polymers P1 and P2 according to the invention and of comparative polymers C1 and C2 is indicated in Table 1. Comparative polymers C1 and C2 have different monomers than monomer M1, which results in units of the formula (1) in the polymer.

Example 4

Production of PLEDs

The polymers are investigated for use in PLEDs. The PLEDs are in each case two-layer systems, i.e. substrate// ITO//PEDOT//polymer//cathode. PEDOT is a polythiophene derivative (Baytron P, from H. C. Starck, Goslar). The cathode used in all cases is Ba/Ag (Aldrich). The way in which PLEDs are produced is described in detail in WO 04/037887 and the literature cited therein.

Examples 5 to 8

Device Examples

The results obtained on use of polymers P1 and P2 according to the invention in PLEDs are likewise shown in Table 1. Also shown are the electroluminescence results obtained using comparative polymers C1 and C2.

As can be seen from the results, the efficiency of the polymers according to the invention is better than that of the comparative polymers. The emission colour is comparable and the lifetimes are significantly improved taking this into account. This shows that the polymers according to the invention are more suitable for use in displays than polymers in accordance with the prior art.

TABLE 1

| Example | Polymer | Monomers | Max. eff./ cd/A | U@100 cd/m²/V | CIE x/y[a] | Lifetime[b]/h |
|---|---|---|---|---|---|---|
| 5 | P1 | 10% M1<br>50% M2<br>20% M3<br>10% M4<br>10% M5 | 7.7 | 2.8 | 0.16/0.24 | 400 |
| 6 | P2 | 2% M1<br>50% M2<br>46% M3<br>2% M5 | 6.02 | 3.3 | 0.15/0.19 | 1200 |
| 7 | C1 | 50% M2<br>30% M3<br>10% M4<br>10% M5 | 4.66 | 3.9 | 0.17/0.30 | 180 |
| 8 | C2 | 50% M2<br>46% M3<br>2% M4<br>2% M5 | 4.70 | 4.7 | 0.17/0.26 | 449 |

[a]CIE coordinates: colour coordinates of the Commission Internationale de l'Eclairage 1931
[b]Lifetime; time until the luminance drops to 50% of the initial luminance, initial luminance 400 cd/m²

The invention claimed is:

1. A polymer containing units of the formula (I)

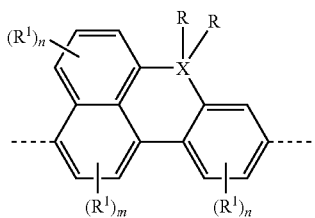

Formula (I)

in which

R is on each occurrence, identically or differently, H, a straight-chain alkyl chain having 1 to 40 C atoms, a branched alkyl chain having 3 to 40 C atoms or a cyclic alkyl chain having 3 to 40 C atoms, each of which is optionally substituted by $R^1$ and in which, in addition, one or more non-adjacent C atoms is optionally replaced by $=N-R^1$, $-O-$, $-S-$, $-O-CO-O-$, $-CO-O-$, $-CR^1=CR^1-$ or $-C\equiv C-$ and in which, in addition, one or more H atoms is optionally replaced by F, Cl, Br, I or CN, or an aromatic ring system having 5 to 40 C atoms or a heteroaromatic ring system having 2 to 40 C atoms, which is optionally substituted by one or more radicals $R^1$; the two radicals R here optionally form a further mono- or polycyclic, aromatic or aliphatic ring system with one another;

$R^1$ is on each occurrence, identically or differently, H, a straight-chain alkyl chain having 1 to 22 C atoms, a branched alkyl chain having 3 to 22 C atoms or a cyclic alkyl chain having 3 to 22 C atoms, in which, in addition, one or more non-adjacent C atoms is optionally replaced by $=N-R^2$, $-O-$, $-S-$, $-O-CO-O-$, $-CO-O-$, $-CR^2=CR^2-$ or $-C\equiv C-$ and in which, in addition, one or more H atoms is optionally replaced by F, Cl, Br, I or CN, or an aryl, heteroaryl, aryloxy or heteroaryloxy group having 5 to 40 C atoms, which is optionally substituted by one or more non-aromatic radicals $R^1$; two or more of the radicals $R^1$ here optionally form a ring system with one another and/or with R; or F, Cl, Br, I, CN, $N(R^2)_2$, $Si(R^2)_3$ or $B(R^2)_2$;

$R^2$ is on each occurrence, identically or differently, H or an aliphatic or aromatic hydrocarbon radical having 1 to 20 C atoms;

X is on each occurrence, identically or differently, B, C, N, O, P, S, Se, P=O, S=O or $SO_2$;

n is on each occurrence, identically or differently, 0, 1, 2 or 3;

m is on each occurrence, identically or differently, 0, 1 or 2; and the dashed bond denotes the link in the polymer and with the proviso that if X is O then there are no Rs present and if X is N or B, then there is only one R present and if X is S or P=O then there can be no Rs present.

2. The polymer according to claim 1, wherein the polymer is a conjugated or partially conjugated polymer and with the proviso that at least one or both of the radicals R is (are) not equal to H.

3. The polymer according to claim 1, wherein the polymer further contains structural elements besides the units of the formula (I).

4. The polymer according to claim 3, wherein the further structural elements enhance the hole-injection and/or -transport properties, and are selected from the group consisting of triarylamine, benzidine, tetraaryl-para-phenylenediamine, triarylphosphine, phenothiazine, phenoxazine, dihydrophenazine, thianthrene, dibenzo-para-dioxin, phenoxathiyne, carbazole, azulene, thiophene, pyrrole or furan derivatives or further O-, S- or N-containing heterocycles having a high HOMO.

5. The polymer according to claim 3, wherein the further structural elements enhance the electron-injection and/or -transport properties, and are selected from the group consisting of pyridine, pyrimidine, pyridazine, pyrazine, oxadiazole, quinoline, quinoxaline, phenazine derivatives, or triarylboranes or further O-, S- or N-containing heterocycles having a low LUMO.

6. The polymer according to claim 3, wherein the further structural elements are triarylamine, benzidine, tetraaryl-para-phenylenediamine, triarylphosphine, phenothiazine, phenoxazine, dihydrophenazine, thianthrene, dibenzo-para-dioxin, phenoxathiyne, carbazole, azulene, thiophene, pyrrole, furan derivatives, O-, S- or N-containing heterocycles having a high HOMO, pyridine, pyrimidine, pyridazine, pyrazine, oxadiazole, quinoline, quinoxaline, phenazine derivatives, triarylboranes or O-, S- or N-containing heterocycles having a low LUMO or a mixture thereof.

7. The polymer according to claim 3, wherein the further structural elements modify the emission characteristics to such an extent that electrophosphorescence can be obtained instead of electrofluorescence.

8. The polymer according to claim 3, wherein the further structural elements improve the transition from the singlet state to the triplet state are selected from the group consisting of classes of the carbazole and bridged carbazole dimer units, ketones, phosphine oxides, sulfoxides, sulfones and silane derivatives.

9. The polymer according to claim 3, wherein the further structural elements influence the morphology and/or emission color of the polymer are selected from the group consisting of 1,4-phenylene, 1,4-naphthylene, 1,4-anthrylene, 9,10-anthrylene, 1,6-pyrenylene, 2,7-pyrenylene, 4,9-pyrenylene, 3,9-perylenylene, 3,10-perylenylene, 4,4'-biphenylylene, 4,4''-terphenylylene, 4,4'-bi-1,1'-naphthylylene, 4,4'-tolanylene, 4,4'-stilbenzylene and 4,4''-bisstyrylarylene derivatives.

10. The polymer according to claim 3, wherein the further structural elements which are used as backbone are selected from the classes of the 4,5-dihydropyrene derivatives, 4,5,9,10-tetrahydropyrene derivatives, fluorene derivatives, 9,9'-spirobifluorene derivatives, 9,10-dihydrophenanthrene derivatives, 5,7-dihydrodibenzooxepine derivatives and cis- and trans-indenofluorene derivatives.

11. The polymer according to claim 1, wherein the proportion of the units of the formula (1) is at least 5 mol %.

12. The polymer according to claim 1, wherein the units of the formula (I) are bonded in the polymer via a 3,9-link.

13. The polymer according to claim 1, wherein

R is on each occurrence identical or different and stands for a straight-chain alkyl chain having 1 to 25 C atoms, a branched alkyl chain having 3 to 25 C atoms or a cyclic alkyl chain having 3 to 25 C atoms, in which, in addition, one or more non-adjacent C atoms is optionally replaced by =N—R', —O—, —S—, —O—CO—O—, —CO—O—, —CH=CH— or —C≡C— and in which, in addition, one or more H atoms is optionally replaced by F or CN, or an aromatic or heteroaromatic group having 4 to 20 C atoms, which is optionally substituted by one or more non-aromatic radicals $R^1$; the two radicals R here optionally form a further mono- or polycyclic, aromatic or aliphatic ring system with one another;

$R^1$ is on each occurrence identical or different and stands for H, a straight-chain alkyl chain having 1 to 22 C atoms, a branched alkyl chain having 3 to 22 C atoms or a cyclic alkyl chain having 3 to 22 C atoms, in which, in addition, one or more non-adjacent C atoms is optionally replaced by =N—$R^2$, —O—, —S—, —O—CO—O—, —CO—O—, —CH=CH— or —C≡C— and in which, in addition, one or more H atoms is optionally replaced by F or CN, or an aryl, heteroaryl, aryloxy or heteroaryloxy group having 5 to 40 C atoms, which is optionally substituted by one or more non-aromatic radicals $R^1$; two or more of the radicals $R^1$ here optionally form a mono- or polycyclic, aliphatic or aromatic ring system with one another and/or with R; or F, Cl, Br, I, CN, $N(R^2)_2$, $Si(R^2)_3$ or $B(R^2)_2$; and X is on each occurrence identical or different and stands for B, C, N, O, P, S, P=O, S=O or $SO_2$.

14. A mixture of one or more polymers according to claim 1 with further polymeric, oligomeric, dendritic and/or low-molecular-weight substances.

15. A solution or a formulation which comprises at least one or more polymers according to claim 1 in one or more solvents.

16. A light-emitting diode which comprises the polymer according to claim 1.

17. An organic electronic component which comprises one or more active layers, wherein at least one of the active layers comprises one or more polymers according to claim 1.

18. The organic electronic component according to claim 17, wherein the component is a polymeric light-emitting diode (PLED), organic integrated circuit (O-IC), organic field-effect transistor (OFET), organic thin-film transistor (OTFT), organic solar cell (O-SC) or organic laser diode (O-laser).

19. The organic electronic component according to claim 18, wherein the component is a polymeric light-emitting diode.

* * * * *